(12) United States Patent
Jimenez et al.

(10) Patent No.: US 8,397,910 B2
(45) Date of Patent: Mar. 19, 2013

(54) POWERED TOOTHBRUSH PACKAGE

(75) Inventors: Eduardo J. Jimenez, Manalapan, NJ (US); Alberto Mantilla, Rego Park, NY (US); Tony Baxter, Hoboken, NJ (US); Pablo Andres Ramirez Lozano, Rego Park, NY (US); Marisol Rodriguez Perez, Brooklyn, NY (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/089,110

(22) Filed: Apr. 18, 2011

(65) Prior Publication Data

US 2011/0192752 A1    Aug. 11, 2011

Related U.S. Application Data

(62) Division of application No. 12/051,083, filed on Mar. 19, 2008, now Pat. No. 7,992,710.

(51) Int. Cl.
*B65D 83/10* (2006.01)
*B65D 85/00* (2006.01)

(52) U.S. Cl. ................ 206/362.2; 206/459.1; 206/459.5

(58) Field of Classification Search ............... 206/362.2, 206/320, 361, 420, 418, 419, 421, 422, 730, 206/731, 732, 733, 734, 735, 459.1, 459.5; 446/268, 73, 74, 75, 76
See application file for complete search history.

(56) References Cited

U.S. PATENT DOCUMENTS

| | | | |
|---|---|---|---|
| 3,811,213 A | 5/1974 | Eaves | |
| 4,668,597 A | 5/1987 | Merchant | |
| 4,976,620 A | 12/1990 | Tacquard et al. | |
| 5,142,384 A | 8/1992 | Wood et al. | |
| 5,494,252 A | 2/1996 | Amit et al. | |
| 5,525,383 A | 6/1996 | Witkowski | |
| 5,586,089 A | 12/1996 | McGarvey | |
| 6,070,724 A | 6/2000 | McCool | |
| 6,084,526 A | 7/2000 | Blotky et al. | |
| 6,749,437 B2 | 6/2004 | Chan | |
| 6,932,216 B2 | 8/2005 | Blaustein et al. | |
| 2002/0020645 A1 | 2/2002 | Blaustein et al. | |
| 2002/0104240 A1 | 8/2002 | Howell et al. | |
| 2003/0066145 A1 | 4/2003 | Prineppi | |
| 2004/0245765 A1 | 12/2004 | Taylor et al. | |
| 2006/0207901 A1 | 9/2006 | Sorrentino | |
| 2007/0041611 A1 | 2/2007 | Hersch et al. | |

FOREIGN PATENT DOCUMENTS

| JP | 2007/030967 | 2/2007 |
|---|---|---|
| WO | WO 02/101669 | 12/2002 |
| WO | WO 2006/096628 | 9/2006 |

OTHER PUBLICATIONS

Moire pattern—http://en.wikipedia.org/wiki/Moir%C3%A9_pattern—pp. 1-7.
International Search Report from the European Patent Office, dated Dec. 10, 2008, for corresponding International Application No. PCT/US2008/057466.

*Primary Examiner* — J. Gregory Pickett
*Assistant Examiner* — Ernesto Grano
(74) *Attorney, Agent, or Firm* — Judy W. Chung

(57) ABSTRACT

An oral care implement demonstration assembly includes a powered oral care implement, a package housing and a plurality of demonstration elements. The oral care implement demonstration assembly is configured to produce a visual demonstration effect when relative movement is provided between a first demonstration element and a second demonstration element. Among the visual effects that may be utilized is a Moiré effect. Additionally, an associated method for demonstrating features of an oral care implement though one or more visual effects is described herein.

12 Claims, 14 Drawing Sheets

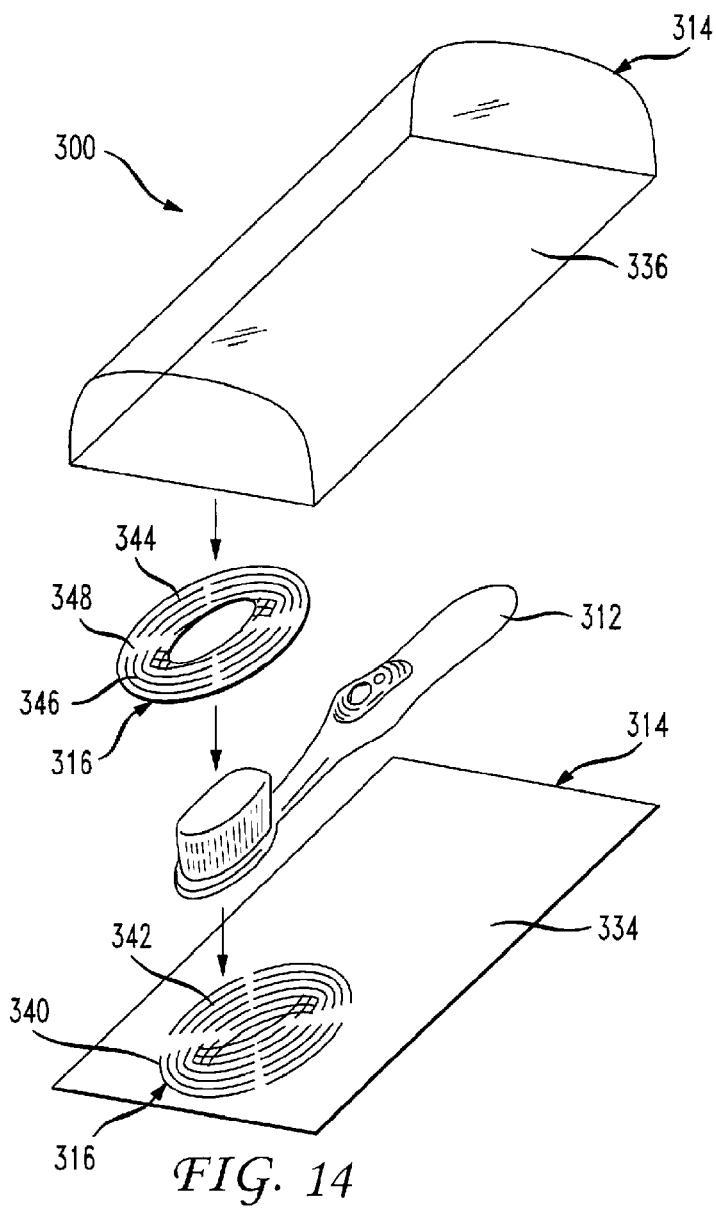
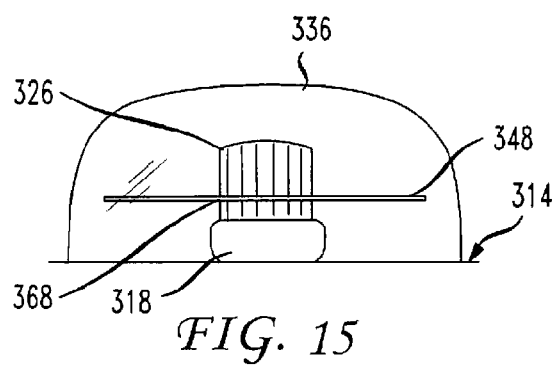
FIG. 14
FIG. 15

POWERED TOOTHBRUSH PACKAGE

CROSS-REFERENCE TO RELATED APPLICATIONS

This application is a divisional application of U.S. patent application Ser. No. 12/051,083 filed Mar. 19, 2008, the contents of which are expressly incorporated herein by reference.

BACKGROUND OF THE INVENTION

The present invention relates to a package in general, and more particularly to a powered toothbrush package that visually demonstrates the functionality of a toothbrush. Consumers generally use various sensing capabilities including sight, sound and touch in making a determination as to the desirability of a product. However, at a point of purchase such as a retail location, products may not be completely accessible to a consumer because the products may be housed, contained or otherwise wrapped in packaging to protect against loss or damage.

Furthermore, it is often difficult for consumers to understand and correlate how movement of a powered toothbrush head results in cleaning teeth. Hence, there is a need for product packaging and methods for demonstrating the functionality of a powered toothbrush to a consumer in an easily perceivable fashion.

BRIEF SUMMARY OF THE INVENTION

The present invention pertains to a package for a powered product. In one aspect, a powered toothbrush package visually demonstrates the functionality of a toothbrush.

According to one aspect of the invention, a powered toothbrush package may take the form of an oral care implement vibration demonstration assembly. In addition, the assembly may incorporate an associated method for demonstrating features of an oral care implement.

According to one aspect of the invention, a package for an oral care implement has a base member having indicia associated therewith. The indicia are structured such that in response to a vibratory input adapted to be provided by the implement, a visual effect is produced from the indicia. In one construction, the indicia include a first element containing a marking and a second element containing a marking. Relative movement is provided between the elements that cause the markings to provide a visual effect to a viewer. In one exemplary construction, the relative movement is provided in response to a vibratory input provided by the oral care implement.

Another aspect of the invention is directed to an oral care implement vibration demonstration assembly that includes a powered oral care implement, a package housing, and a plurality of vibration demonstration elements as described herein. The oral care implement demonstration assembly may be configured to produce a visual demonstration effect when a first vibration demonstration element is moved relative to a second vibration demonstration element. A Moiré effect is among the visual effects that may be provided by the demonstration assembly.

Another aspect of the invention is directed to an oral care implement demonstration assembly that includes a powered toothbrush having a user input, a product package, a visual demonstration insert that has visual elements and a visual demonstration reference element. Further, a portion of the visual demonstration insert may visually overlay a portion of the visual demonstration reference element as movement of one relative to the other causes a visual effect.

A further aspect of the invention is directed to a method for demonstrating vibration of an oral care implement. A package is provided that contains a powered oral care implement having a user input. A first demonstration element and a second demonstration element are operably associated with the package and the implement. The method includes vibrating the oral care implement via the user input and providing relative movement between the first demonstration element and the second demonstration element to produce a visual effect.

According to another aspect of the invention, the method may include producing multiple visual effects by moving multiple vibration demonstration elements relative to other vibration demonstration elements to produce various visual effects including simultaneously providing visual effects such as a combination of Moiré effects and movement of a visual illustration in the form of a toothbrush.

Accordingly, aspects of the present invention provides product packaging that can effectively convey features, components and/or potential uses of a product to a potential consumer at a point of sale. Hence, consumers will often feel more comfortable purchasing a product that they have seen demonstrated in an illustrative use environment. With the principles of the present invention, conveyance of product attributes and demonstration of the use of the product is possible utilizing product packaging.

Other features and advantages of the invention will be apparent from the following description taken in conjunction with the following drawings.

BRIEF DESCRIPTION OF THE DRAWINGS

FIG. 14 is a perspective view of another construction of a toothbrush and package assembly of the present invention;

FIG. 15 is an end view of the toothbrush and package assembly shown in FIG. 14 and including a cover;

DETAILED DESCRIPTION OF THE INVENTION

Several constructions of a package assembly are disclosed in FIGS. 1-26. The constructions may include oral care implements, such as toothbrushes, tongue cleaners and other related apparatus, which are typically displayed for purchase within product packaging.

Figure 1:
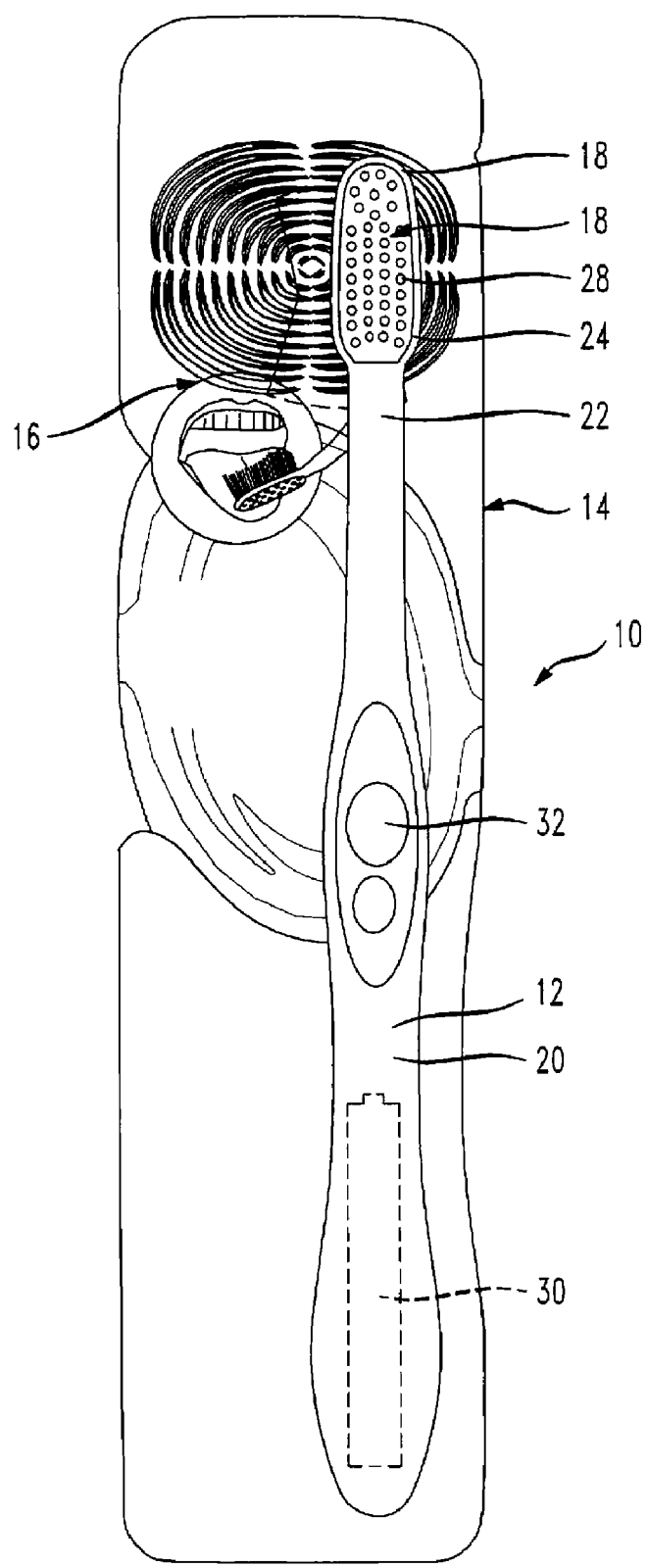
FIG. 1 is a schematic front view of a powered toothbrush package according to the present invention that may take the form of an oral care implement demonstration assembly.

In certain exemplary constructions such as shown in FIG. 1, the package assembly is used to contain an oral care implement such as a powered toothbrush. As described in greater detail below, the package assembly utilizes relative movement of indicia to provide unique visual features. It is understood that the principals of the present invention can also be used with various other types of products wherein the products utilize the indicia to provide visual effects.

Figure 2:
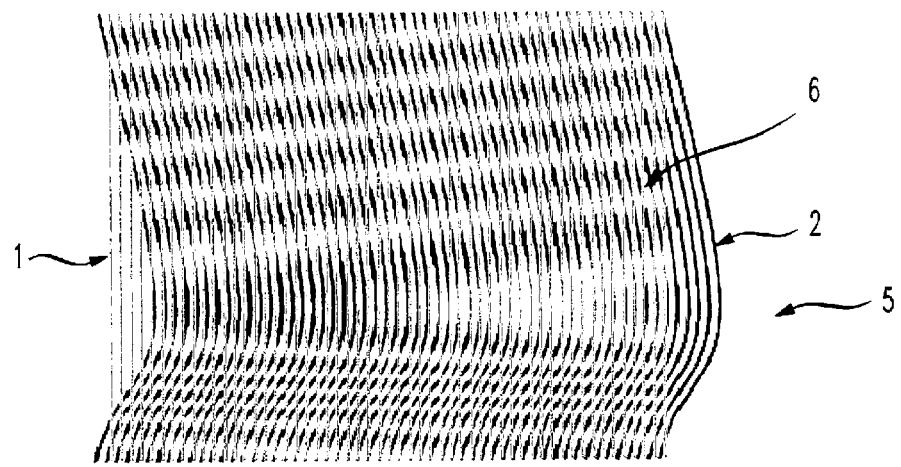
FIG. 2 is an illustrative example of a Moiré pattern utilized in the present invention.
Figure 3:
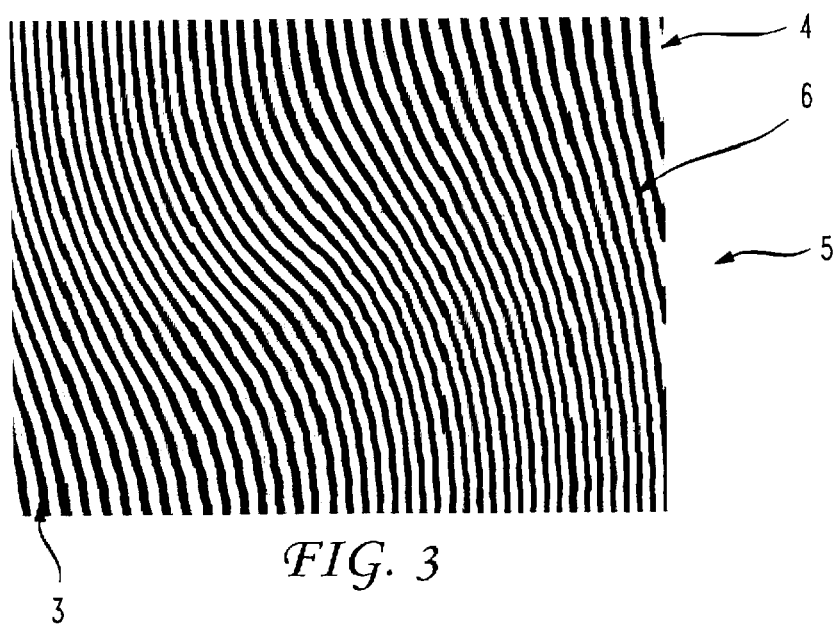
FIG. 3 is an illustrative example of another Moiré pattern utilized in the present invention.

FIGS. 2 and 3 illustrate a concept of superimposing a repetitive design (such as a grid of lines) on the same or a different design, to produce a pattern distinct from its separate component designs. An appearance of a new set of lines passing through the points where the original lines cross at small angles may be created so that the human eye is enabled to perceive a distortion or flickering of indicia, such as printed or displayed high-contrast images. In FIG. 2 for example, a first set of lines 1 is superimposed over a second set of lines 2. Similarly in FIG. 3, a first set of lines 3 is superimposed over a second set of lines 4. It can be seen that the respective sets of lines in FIGS. 2 and 3 are in different forms. As is apparent from FIGS. 2 and 3, superimposition of these respective sets of lines creates a visual perception to the human eye. This visual perception or effect is commonly referred to as a Moiré effect 5. Accordingly, each set of lines 1, 2, 3, 4 positioned to create the Moiré effect 5 may be referred to as a Moiré pattern 6. The Moiré effect 5 can occur when two or more sets of lines, dots or related structures differ in relative size, angle, spacing or the like.

In FIG. 2, the first set of lines 1 may be described as vertical lines in parallel, and the second set of lines 2 may be described as wavy lines. The first set of lines 1 is superimposed on the second set of wavy lines 2. This contrast in curvature creates the visual Moiré effect 5 as described. The Moiré effect 5 is also created in FIG. 3 when two sets of curved lines 3, 4 are superimposed on one another. Although both sets of lines 3, 4 in FIG. 3 may generally be described as curved lines, the sets of lines 3, 4 possess different specific features including location and size of curvature. When these two sets of lines 3, 4 are superimposed on one another, this superimposed variance in features is detected by the human eye so as to create the Moiré effect 5 as is apparent when viewing FIG. 3. It is understood that the respective sets of lines 1, 2, 3, 4 produce different Moiré effects 5 as can be appreciated when viewing FIGS. 2 and 3. It is further understood that other Moiré effects 5 using other indicia in accordance with the present invention are possible, including other effects shown in the additional figures as described in greater detail below.

This described Moiré effect 5 may in certain instances be generated in nature such as when an observer looks though a window screen and views another window screen or a background of a certain characteristic. The Moiré effect 5 may also be purposely generated using photographic, graphical and/or electronic reproduction means as is well known in the art.

By causing and manipulating the Moiré effect 5 and using other visualization principles and techniques, improved product packaging, demonstration and display is possible. Accordingly, preferred methods of demonstrating use of a product such as an oral care implement and preferred environments for demonstrating uses of the oral care implement are also possible.

FIGS. 1 and 4-6 generally disclose an exemplary construction of a package assembly of the present invention, generally designated with the reference numeral 10. In certain constructions, the package assembly 10 may also be referenced as an oral care implement vibration demonstration assembly 10. As explained in greater detail below, the package assembly 10 generally includes a contained product 12, such as an oral care implement that may be in the form of a powered toothbrush, a package 14 and indicia 16 operably associated with the contained product 12 and/or the package 14. The indicia 16 can take many different forms including being included on additional members such as an insert or demonstration element as further described below.

As discussed, in one exemplary construction of the present invention, the contained product 12 is an oral care implement. The oral care implement may take the form of a powered toothbrush. Various powered toothbrushes are well known in the art, including battery powered toothbrushes.

The powered toothbrush 12 includes a head 18, a body 20 and a neck 22 connecting the head 18 to the body 20. The head 18 further includes a base support 24 and a cleaning member 26 including a plurality of cleaning elements 28. The cleaning elements 28 may include bristles or other known components used in cleaning the oral cavity. The cleaning elements 28 may be made of various polymers, nylons and/or other well known materials commonly used to assist in cleaning of an oral cavity including the teeth, gums and tongue. The base support 24 serves as a supporting structure for the cleaning elements 28. In addition, the base support 24 is configured to move the cleaning elements 28 in response to a user input provided to the toothbrush 12 as described below.

Powered toothbrushes 12 may include cleaning members 26 that rotate, vibrate, oscillate or translate. The cleaning elements 28 may take the form of bristles such as in a standard toothbrush or bristles arranged on one or more rotating, vibrating, oscillating or translating components on the base support 24 as is known in the art. Alternatively, the cleaning member 26 such as the one shown in FIGS. 1 and 4 may be vibrated or moved in one or more axial directions. Combinations of translation, vibration and/or rotation may also be implemented.

A powered drive mechanism and an associated power source are typically housed within the body 20 of the oral care implement. For example, the toothbrush 12 may be compatible with and/or utilize one or more of alkaline or various types of known rechargeable batteries 30 (FIG. 1) capable of powering the toothbrush 12. A motor or other known power generating mechanism (not shown) is linked to the cleaning member 26 and drives the cleaning member 26 in various manners as discussed. Accordingly, the cleaning member 26 may be rotated, vibrated, or oscillated for oral care instruments of varying types. The description of the movement capabilities of the oral care implement 12, including the movement characteristics of the cleaning member 26 and the cleaning elements 28, is for illustration and convenience in a non-limiting manner.

The body 20 and the neck 22 of the toothbrush may be formed from a unitary piece or multiple components. The base support 24 of the head 18 may also be formed as part of a unitary toothbrush 12. A toothbrush grip may be part of the body 20 and formed of a number of features and further may have a surface that improves the ability of the toothbrush to be gripped by human fingers. Grip enhancing elements may also be applied including grip regions and roughened or grooved surfaces.

Figure 4:
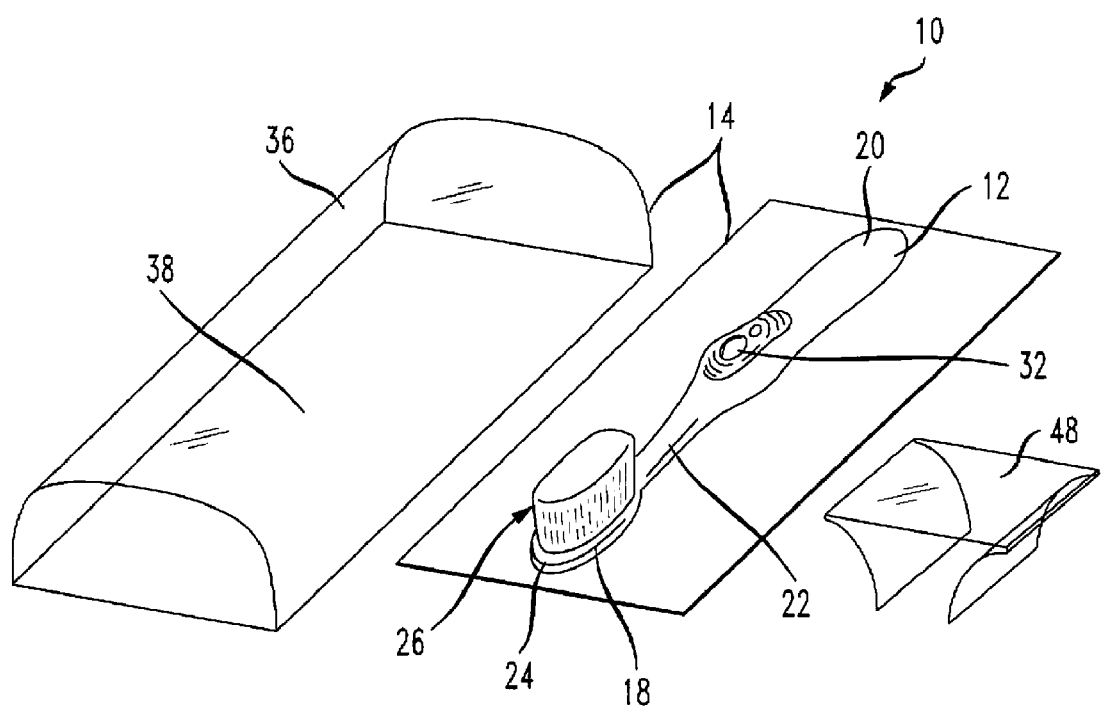
FIG. 4 is a perspective view of a toothbrush and components of a toothbrush package assembly of the present invention.

As further shown in FIGS. 1 and 4, a user input 32 in the form of a depressible button is utilized in turning the powered toothbrush 12 to the "On" position and the "Off" position as is known. The user input 32 may include depressible buttons, switches, dials, slides, knobs and numerous other activation components that may be utilized to change the state of a device between the "On" and "Off" positions.

As further shown in FIGS. 1 and 4-6, the package 14 is provided to contain the toothbrush 12. The package 14 can take various forms and generally has a housing to contain the product. The package 14 includes a base member 34 and a cover 36 in one exemplary construction. The base member 34 is a panel-like member and generally supports the toothbrush 12 by serving as a backing member for the toothbrush 12. The base member 34 may be formed of a number of shapes, dimensions and materials. In certain constructions, the base member 34 may include a cutout for the toothbrush 12 to permit tighter product packaging.

Figure 5:
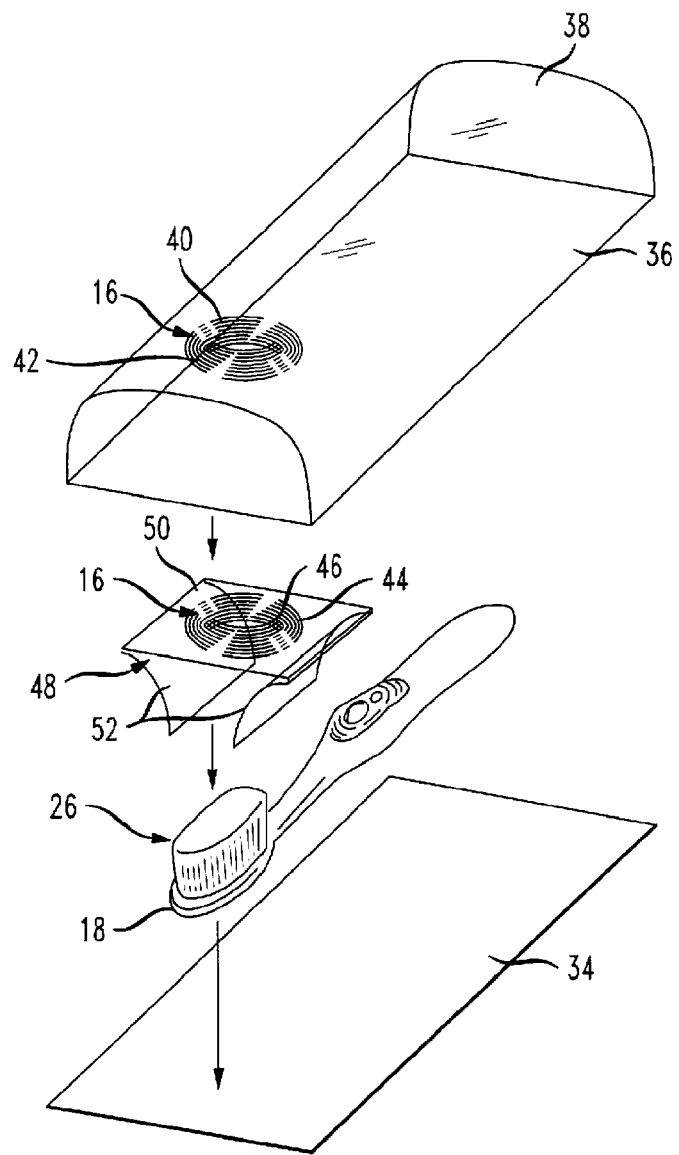
FIG. 5 is an exploded view of the toothbrush and package assembly shown in FIG. 4.
Figure 6:
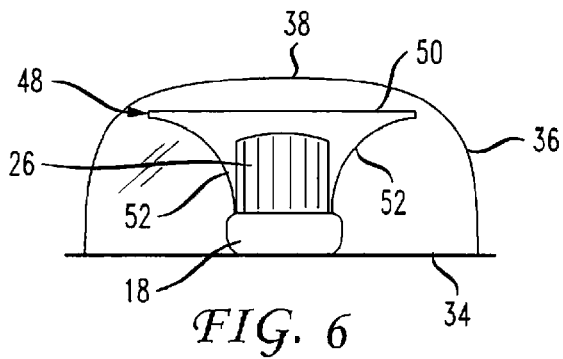
FIG. 6 is an end view of the toothbrush and package assembly shown in FIG. 4 wherein the toothbrush is contained within the package.

The cover 36 of the package 14 is attached to the base member 34 to house or contain the toothbrush 12 in the package 14. The cover 36 may be of a translucent or transparent material wherein a purchaser can view the contents or at least a portion of the contents without opening or damaging the package 14. As shown in FIGS. 4-6, the cover 36 has an arched segment 38 to provide clearance to fit over the oral care implement 12 housed between the base member 34 and the cover 36. The cover 36 may take various specific shapes and configurations and may also be omitted from the product packaging. The cover 36 may also house or support portions of the indicia 16 as described in greater detail below. Further, instructional and informational materials may also be housed within the package 14 such as between the base member 34 and the cover 36 and particularly fit along an interior surface of the cover 36.

As can be appreciated from FIGS. 4-6, the toothbrush 12 is contained within the package 14 and can be viewed by a consumer through the transparent cover 36. As described in greater detail below, the indicia 16 may be operably associated with the package 14 including one or both of the base member 34 and the cover 36.

As discussed, the powered toothbrush package 10 further includes the indicia 16. For clarity, the indicia 16 are omitted from FIG. 4 but are shown in FIG. 5. The indicia 16 can take many different forms and can be operably associated with various structures of the package assembly 10 including the base member 34, the cover 36 and the toothbrush 12 depending on the desired visual effect to be produced. As further shown in FIG. 5, the indicia 16 may include a first demonstration element 40 having a first marking 42 and a second demonstration element 44 having a second marking 46. In this construction, the first demonstration element 40 is positioned on the cover 36 and in one preferred construction, this portion of the indicia 16 is printed directly onto the cover 36. This demonstration element 40 may be considered a visual demonstration reference element 40. Also, the second demonstration element 44 is included on a separate member which may be referred to as an insert 48 as the insert 48 is a separate member from the basic package components. The insert 48 may be considered a visual demonstration insert 48. The insert 48 has a generally planar top panel 50 having the second marking 46 thereon. The insert 48 further has a pair of depending side panels 52. The side panels 52 have an inward arcuate shape to facilitate attachment to the head 18 as described in greater detail below. In this construction, the second demonstration element 44 is operably associated with the toothbrush 12 and positioned beneath the first demonstration element 40. The demonstration elements 40, 44 can be positioned at different locations on the package 14. As can be appreciated from FIG. 5, the first demonstration element 40 and the second demonstration element 44 have complementary markings 42, 46 of similar design. The markings 42, 46 making up the indicia 16, however, may be any visually perceivable elements including sets of lines, dots, symbols designs, figures, graphical illustrations, pictures, symbols, colored elements, and specific Moiré markings or Moiré patterns. The indicia 16 are structured to provide a visual effect to a consumer viewing the package assembly 10.

As shown in FIGS. 5 and 6, the individual components are attached to form the package assembly 10. As discussed with respect to this construction, the second demonstration element 44 is operably associated with the toothbrush 12. In one exemplary configuration, the insert 48 is connected to the toothbrush 12 wherein the side panels 52 are attached to the head 18 via an adhesive or other known attachment methods. The insert 48 is removably attached wherein a consumer can remove the insert 48 after opening the package 14 after purchase. As shown in FIG. 6, the top panel 50 is positioned over the cleaning member 26. The toothbrush 12 with the attached second demonstration element 44 is then attached or otherwise supported by the base member 34 of the package 14. The cover 36 is then positioned over the toothbrush 12 and attached to the base member 34 by known attachment methods. As can be appreciated from FIGS. 5 and 6, the first demonstration element 40 with the first marking 42 is positioned over the second demonstration element 44 with the second marking 46. Thus, the markings 42, 46 are in a visually overlapping configuration, or in superimposed relation. The markings 42, 46 can also be aligned or slightly offset or staggered if desired. More specifically, from at least one vantage point exterior to the package assembly 10, an observer would perceive at least a portion of the demonstration elements 40, 44 overlapping. The first marking 42 is complementary to the second marking 46, so that taken together, the elements 40, 44 provide a visual effect to a consumer viewing the package assembly 10.

An enhanced visual effect and visual demonstration can be provided by moving the demonstration elements 40, 44 relative to one another thereby further manipulating the superimposed markings. For example, the demonstration elements 40, 44 are moved relative to one another in various speeds, patterns and directions to create desired visual effects and, as later described, to include a visual effect that demonstrates features of an oral care implement. Generally, this relative movement may be accomplished by moving one of the demonstration elements 40, 44 and keeping the other element in a stationary position when viewed with the package 14 as a point of reference. Alternatively, both demonstration elements 40, 44 may be moved in relation to the package 14, often in associated or complimentary fashion.

In one exemplary construction, a visual effect produced from relative motion relies on a user input provided to the toothbrush 12 wherein the package assembly 10 may be referred to as an oral care implement vibration demonstration assembly 10. A consumer can press the user input 32 through the cover 36 to activate or vibrate the toothbrush 12. Vibration is one exemplary form of movement. Upon activation, the head 18 and cleaning member 26 vibrate and therefore move. Because the second demonstration element 44 is attached to the head 18, the second demonstration element 44 also moves from the vibration. Thus, in response to the user input causing vibration, there is relative movement between the second demonstration element 44 and the first demonstration element 40. This relative movement between the components of the indicia 16 produces an active, dynamic visual effect to the consumer. In this configuration, the demonstration elements 40, 44 may be referred to as vibration demonstration elements. The first demonstration element 40 remains stationary, and this element is considered the visual demonstration reference element. This configuration could be reversed if desired wherein the first demonstration element 40 could be configured for movement while the second demonstration element 44 could become stationary as a reference element. It is also understood that both demonstration elements 40, 44 could be configured for movement if desired. Although an enhanced visual effect is produced by relative movement of the indicia components, it is understood that the indicia 16 could also take the form of a single Moiré pattern (e.g., FIGS. 2 and 3) that is operably associated with the package 14. The indicia 16 in this form having overlapping designs could be printed on the base member 34 or the cover 36 to produce a visual effect for the viewer.

Figure 7:
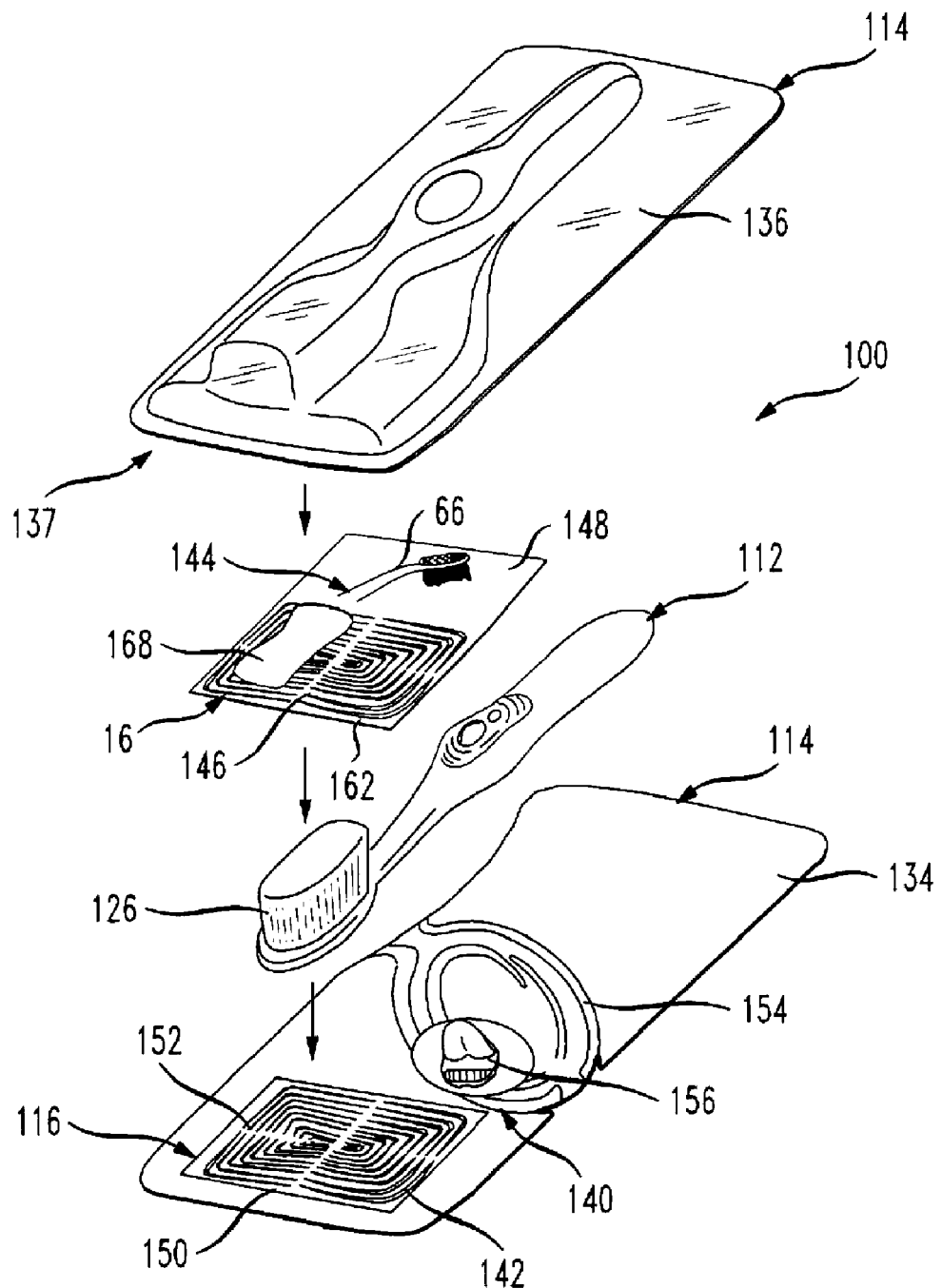
FIG. 7 is a front view of another construction of the present invention showing a toothbrush and components of a toothbrush package assembly.

FIGS. 7-11 disclose another exemplary construction of the present invention. The construction of FIGS. 7-11 is similar to the construction of FIGS. 4-6 and similar components will be designated using similar reference numerals in a 100 reference numeral series. As shown in FIG. 7, a package assembly 100 generally includes a powered toothbrush 112, a package 114 and indicia 116 operably associated with the toothbrush 112 and the package 114. As discussed, the indicia 116 can take many different forms and in this construction, the indicia 116 include additional features that produce further visual effects providing even greater impact to a viewer.

The toothbrush 112 is substantially identical to the toothbrush 12 of FIGS. 4-5 and the above description is applicable to this construction. Likewise, the package 114 is similar to the package 14 of FIGS. 4-6 and generally includes a housing formed by the base member 134 and the cover 136. The cover 136 is shaped and dimensioned to define a cavity 137 that generally corresponds to the shape of the toothbrush 112. As before, the cover 136 is generally transparent.

Figure 8:
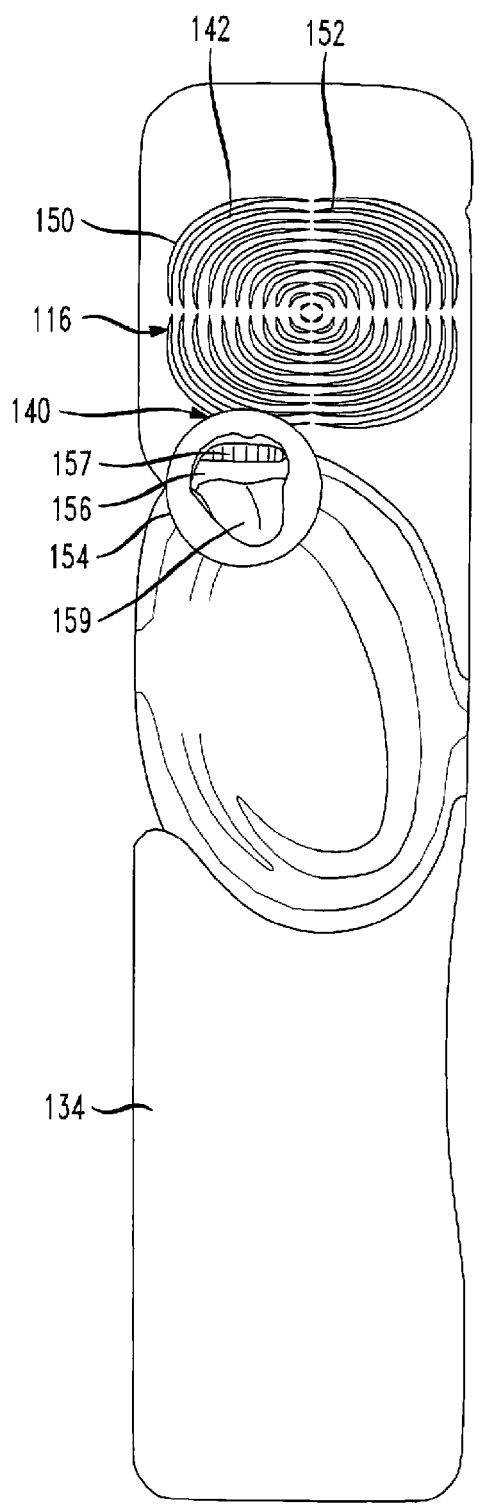
FIG. 8 is a base member of the toothbrush package assembly shown in FIG. 7.
Figure 9:
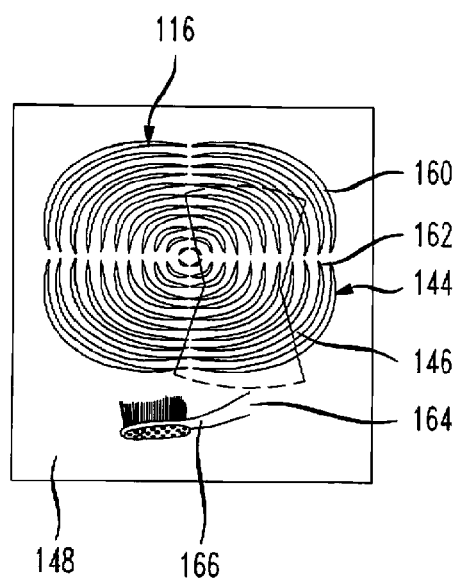
FIG. 9 is a movable element of the toothbrush package assembly shown in FIG. 7.

FIGS. 7-9 further show the indicia 116 operably associated with the package assembly 100. In this particular exemplary construction, the indicia 116 are associated with the base member 134 and the toothbrush 112. As further shown in FIGS. 7 and 8, the indicia 116 includes a first demonstration element 140 having a first marking 142 and a second demonstration element 144 having a second marking 146. In this construction, the first demonstration element 140 is positioned on the base member 134 and in one preferred construction, this demonstration element 140 is printed directly onto the base member 134. This demonstration element 140 may be considered a visual demonstration reference element 140. In addition, the first demonstration element 140 includes a first segment 150 and the first marking 142 includes a first design element 152. As previously discussed, the indicia 116 can include many different elements. These elements can include visual illustrations including photographs, drawings, pictures, symbols, representations, color swaths, graphs and other designs. As further shown in FIGS. 7 and 8, the first demonstration element 140 also includes a second segment 154 having a marking in the form of an oral cavity 156, specifically an open human mouth. The oral cavity 156 includes a depiction of teeth 157 and a tongue 159. The oral cavity 156 is printed directly onto the base member 134. The oral cavity 156 will cooperate with other demonstration elements as described in greater detail below.

The indicia 116 also include the second demonstration element 144 as a separate member in the form of the insert 148. The insert 148 may be considered a visual demonstration insert 148. The insert 148 in this construction is a generally planar member 148 having the second marking 146 thereon. The insert 148 is generally transparent or translucent. In addition, the second demonstration element 144 includes a first segment 160 and the second marking 146 includes a second design element 162. In addition, the second demonstration element 144 also includes a second segment 164 having a marking in the form of a mini-toothbrush 166. The mini-toothbrush 166 will cooperate with the oral cavity 156 as described in greater detail below. The mini-toothbrush 166 may be integral with the design element 162. The insert 148 further includes a cut-out portion 168 dimensioned to receive the head 118 of the toothbrush 112. In one construction, the cut-out portion 168 is generally hour-glass shaped. In FIG. 9, the cut-out portion is represented by boundary lines. The cut-out portion is made through a part of the first design element 152.

As can be appreciated from FIGS. 7-9, the first design element 152 of the first demonstration element 140 and the second design element 162 of the second demonstration element 144 are generally complementary in shape. When the package assembly 100 is assembled, the design elements 152, 162 generally overlap and provide a visual effect in the form of a Moiré effect. The oral cavity 156 and mini-toothbrush 166 also complement one another. As discussed below, these various components of the indicia 116 cooperate to produce visual effects to a consumer viewing the package assembly 100.

Figure 10:
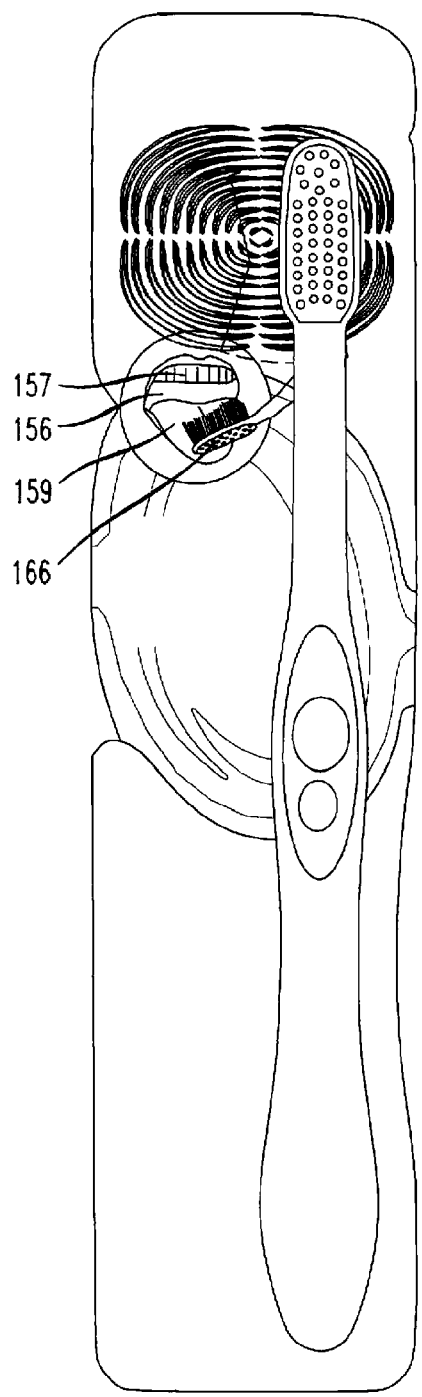
FIG. 10 is a front view of the toothbrush and toothbrush package assembly shown in FIG. 7 that forms an oral care implement vibration demonstration assembly, the assembly being in a deactivated state.
Figure 11:
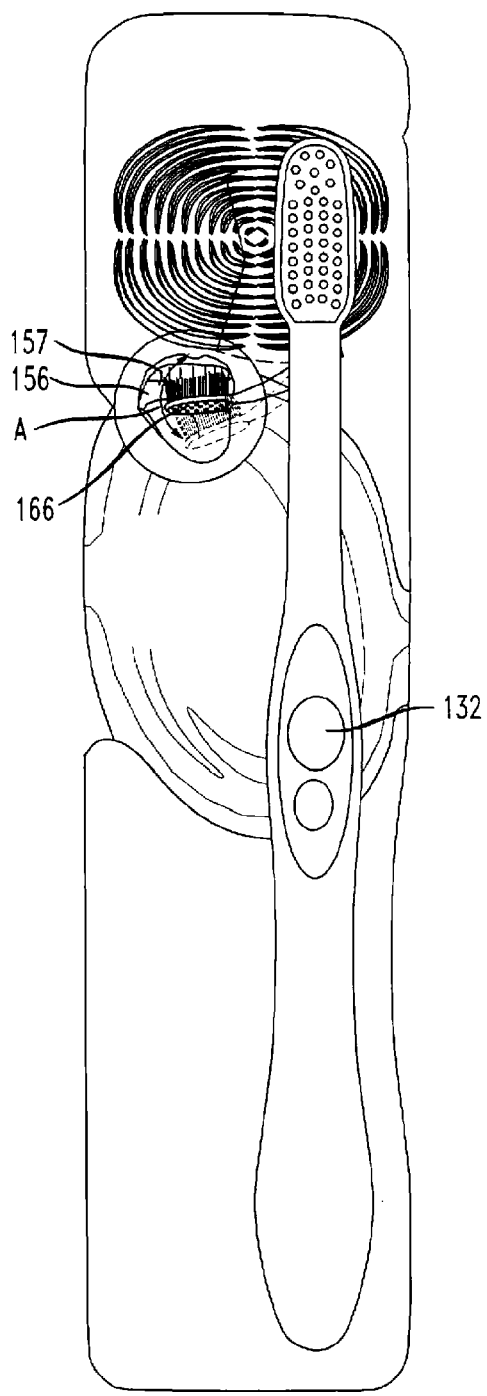
FIG. 11 is a front view of the assembly shown in FIG. 10 wherein the assembly is in an activated state to produce a visual effect.

As can be appreciated from FIGS. 7 and 10-11, the individual components are attached to form the package assembly 100. The second demonstration element 144 is attached to the toothbrush 112 wherein the cleaning member 126 is received by the cut-out portion 168 in an interference fit. The toothbrush 112 is generally attached or supported by the base member 134. The cover 136 is placed over the toothbrush 112 and attached to the base member 134, the toothbrush 112 being received in the cavity 137 of the cover 136. It is noted that the cover 136 is not shown in FIGS. 10 and 11.

As can be appreciated from FIGS. 10 and 11, the second demonstration element 144 is positioned over the first demonstration element 140. In particular, the second design element 162 overlaps the first design element 152 thereby producing a visual effect. The respective lines of the design elements may be considered to be Moiré designs that upon being placed in an overlapping fashion, provide a Moiré pattern. It is understood that the design elements 152, 162 could be aligned or offset in FIG. 10 as desired. As further shown in FIG. 10, the mini-toothbrush 166 is positioned proximate the oral cavity 156. It is further understood that in FIG. 10, the toothbrush 112 is in an inactivated state.

Similar to the previous construction, a further enhanced feature is provided that relies on the user input 132. As shown in FIG. 11, upon pressing the user input 132 through the cover 136, the toothbrush 112 is activated and vibrates. The insert 148 is connected to the head 118 of the toothbrush 112, so that the first design element 152 moves relative to the stationary second design element 162 thereby producing a further visual effect. In addition, in response to the vibration, the mini-toothbrush 166 moves relative to and proximate the stationary oral cavity 156.

In particular, this vibration produces a visual effect of the mini-toothbrush 166 moving towards the teeth 157 as shown by the arrow A. Thus, when the toothbrush 112 is activated, the mini-toothbrush 166 appears to moving within the oral cavity 157 and specifically brushing the teeth 157 in the oral cavity 159. This indicia 116 produces this active visual effect to effectively demonstrate use of the toothbrush 112. As is done in this illustrative example, the visual effect (including the Moiré effect may be designed and chosen so as to visually demonstrate and convey to a consumer the movement and vibration characteristics that may not otherwise be fully apparent to the consumer. Because the toothbrush 112 has specific movement, vibration and oscillation characteristics, Moiré patterns 20 are chosen such that a visual effect is apparent in the activated state as shown in FIG. 11. Upon placing the toothbrush 112 in an inactivated state via the user input 132, the insert 148 including the second design element 162 and the mini-toothbrush 166 return to the position shown in FIG. 10.

FIGS. 12-24 disclose additional exemplary constructions of the package assembly of the present invention. These constructions generally have components similar to the package assemblies in FIGS. 1-13 and similar reference numerals will be used to designate similar components. These constructions also utilize indicia structured and configured to produce visual effects and include numerous variations as to the configurations of the respective package assemblies.

Figure 12:
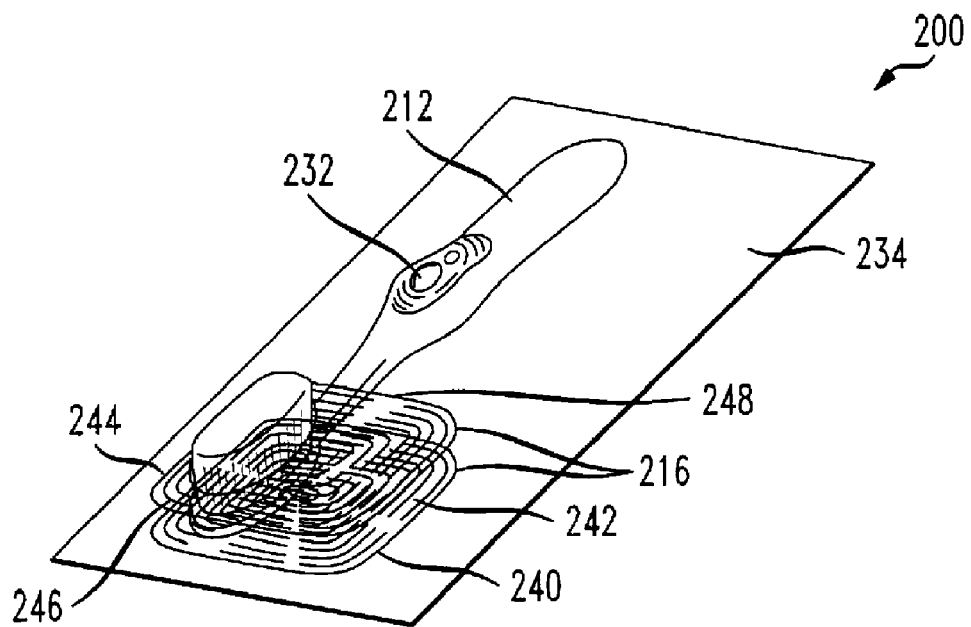
FIG. 12 is a perspective view of another construction of a toothbrush and package assembly of the present invention.
Figure 13:
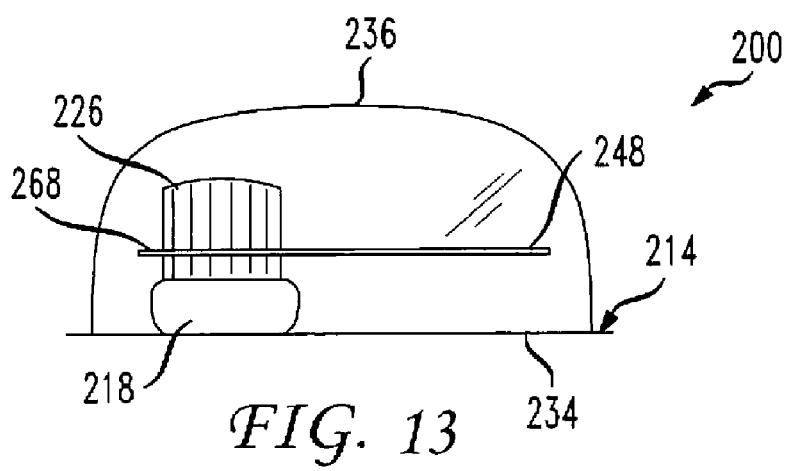
FIG. 13 is an end view of the toothbrush and package assembly shown in FIG. 12 and including a cover.

FIGS. 12 and 13 disclose a packaging assembly 200 having a toothbrush 212, a package 214 and indicia 216. The indicia 216 include a first demonstration element 240 having a first marking 242 that is positioned on the base member 234. The indicia 216 also include an insert 248 having a second demonstration element 244 with a second marking 246 thereon. The insert 248 includes a cut-out portion 268 that is off-center on the insert 248. The demonstration elements 240, 244 have a generally square outer periphery but could have other shapes including a circular shape. Further, the markings 242, 246 are in the form of complimentary swirls or curved lines. The second demonstration element 244 is again attached to the head 218 wherein the cleaning member 226 is received in the cut-out portion 268 so as to frictionally engage the cleaning member 226. The toothbrush 212 is supported by the base member 234 and the cover 236 is attached to the base member 234. As shown, the second demonstration element 244 overlaps the first demonstration element 240 and produces a visual effect. In addition, in response to activating the user input 232, the head 218 vibrates, oscillates, rotates or otherwise moves. Accordingly, the second demonstration element 244 moves relative to the first demonstration element 240 thereby providing additional visual effect.

FIGS. 14 and 15 disclose a packaging assembly 300 having a toothbrush 312, a package 314 and indicia 316. The indicia 316 include a first demonstration element 340 having a first marking 342 that is positioned on the base member 334. The indicia 316 also include an insert 348 having a second demonstration element 344 with a second marking 346 thereon. The insert 348 includes a cut-out portion 368 that is generally centered on the insert 348. The demonstration elements 340, 344 have a generally oval outer periphery but could have other shapes as desired. Further, the markings 342, 346 are in the form of complimentary swirls or curved lines. The second demonstration element 344 is again attached to the head 318 wherein the cleaning member 326 is received in the cut-out portion 368 so as to frictionally engage the cleaning member 326. The toothbrush 312 is supported by the base member 334 and the cover 336 is attached to the base member 334. As shown, the second demonstration element 344 overlaps the first demonstration element 340 and produces a visual effect. In addition, in response to activating the user input 332, the head 318 vibrates. This vibration moves the second demonstration element 344 relative to the first demonstration element 340 thereby providing additional visual effect.

Figure 16:
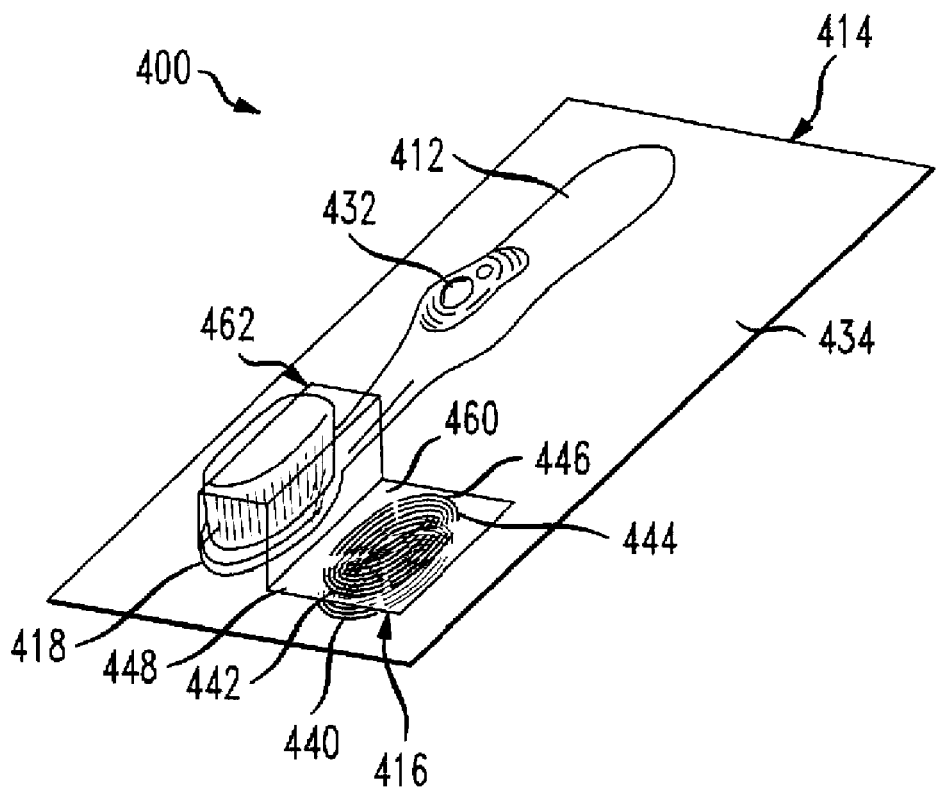
FIG. 16 is a perspective view of another construction of a toothbrush and package assembly of the present invention.
Figure 17:
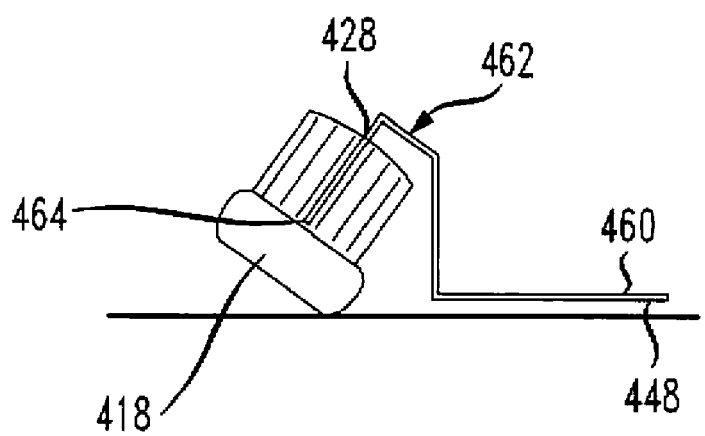
FIG. 17 is an end view of the toothbrush and package assembly shown in FIG. 16.

FIGS. 16 and 17 disclose a packaging assembly 400 having a toothbrush 412, a package 414 and indicia 416. The indicia 416 include a first demonstration element 440 having a first marking 442 that is positioned on the base member 434. The indicia 416 also include an insert 448 having a second demonstration element 444 with a second marking 446 thereon. The second marking 446 is positioned on one segment 460 of the insert 448. An adjacent segment 462 has a plurality of folds defining an end leg 464. The markings 442, 446 are in the form of complimentary swirls or curved lines. The markings 442, 446 are similar in design to the markings in FIGS. 14 and 15. The second demonstration element 444 is again attached to the head 418 wherein the end leg 464 is inserted and embedded into the cleaning member 426 and between the bristles 428. The toothbrush 412 is supported by the base member 434 and it is understood that a cover is attached to the base member 434. As shown, the second demonstration element 444 overlaps the first demonstration element 440 and produces a visual effect. In addition, in response to activating the user input 432, the head 418 vibrates. This vibration moves the second demonstration element 444 relative to the first demonstration element 440 thereby providing additional visual effect.

Figure 18:
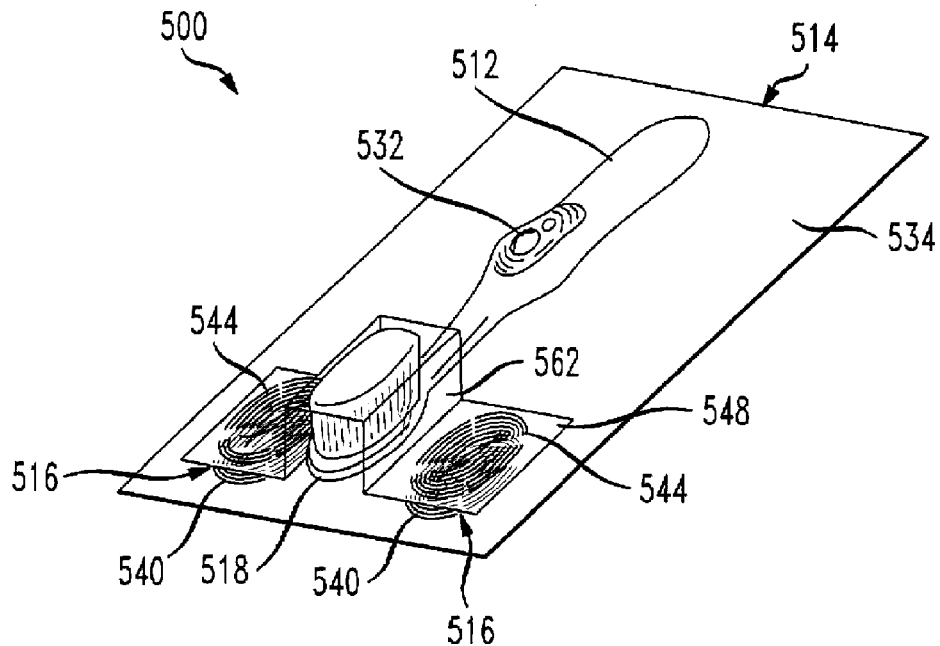
FIG. 18 is a perspective view of another construction of a toothbrush and package assembly of the present invention.
Figure 19:
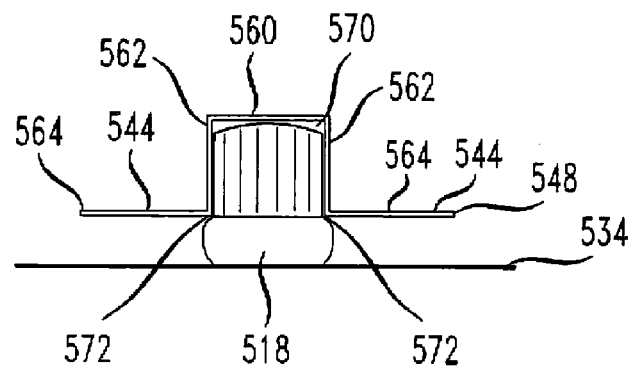
FIG. 19 is an end view of the toothbrush and package assembly shown in FIG. 18.

FIGS. 18 and 19 disclose another construction of a package assembly 500 having a toothbrush 512, a package 514 and indicia 516. The indicia 516 include similar elements as described above. In this construction, first indicia 516a are included on one side of the toothbrush 512 and second indicia 516b are included on the other side of the toothbrush 512. Nevertheless, the indicia can be on one side. The second demonstration element 544 is included on an insert 548. The insert 548 is folded along a length of the insert 548 to define a top panel 560 and side panels 562 that collectively define an insert cavity 570. Winged segments 564 extend from the side panels 562. The second demonstration elements 544 are positioned on the winged segments 564. The insert 548 is attached to the head 518 of the toothbrush 512 wherein the insert cavity 570 receives the cleaning member 526. The insert 548 can be removably attached to the head 518 such as at fold portions 572. It is understood that the indicia 516 include the first demonstration elements 540 and the second demonstration elements 544 configured as described above in generally superimposed and overlapping fashion to produce a visual effect. In addition, upon activation of the toothbrush 512 by pressing the user input 532, the insert 548 moves thereby moving the second demonstration elements 544 relative to the first demonstration elements 540 to produce additional visual effect.

Figure 20:
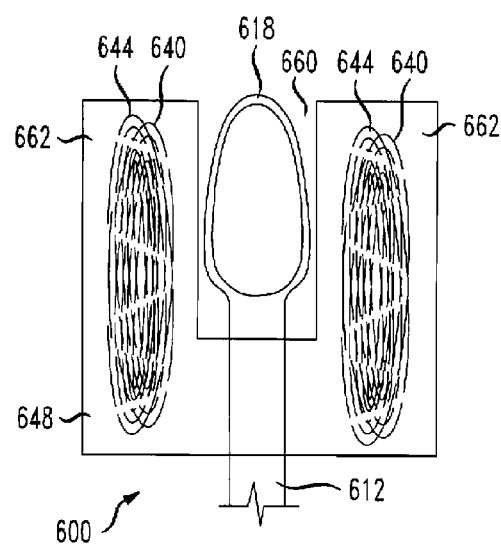
FIG. 20 is a partial front view of another construction of a toothbrush and package assembly of the present invention.
Figure 22:
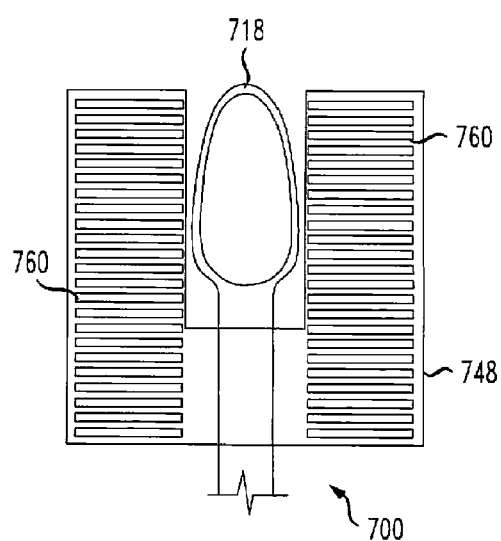
FIG. 22 is a partial front view of another construction of a toothbrush and package assembly of the present invention.
Figure 21:
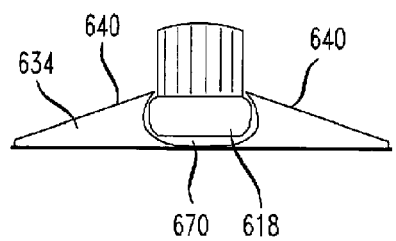
FIG. 21 is an end view of the toothbrush and package assembly of FIG. 20 showing the toothbrush in a base member.
Figure 23:
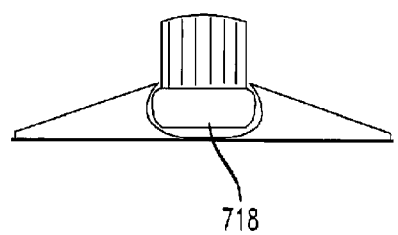
FIG. 23 is an end view of the toothbrush and package assembly of FIG. 22 showing the toothbrush in a base member.
Figure 24:
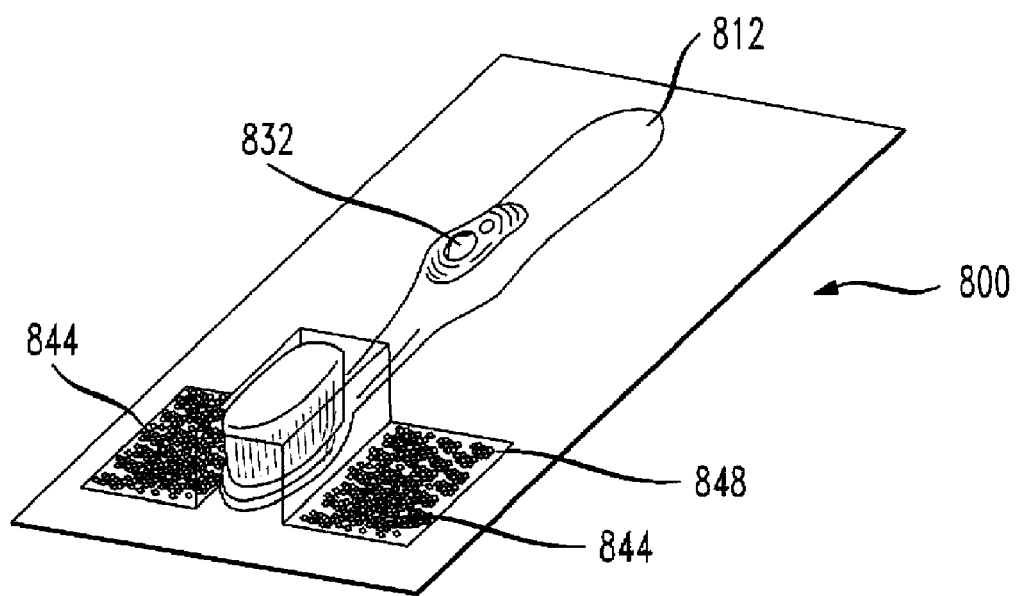
FIG. 24 is a perspective view of another construction of a toothbrush and package assembly of the present invention.

FIGS. 20-23 illustrate further configurations of the package assembly of the present invention. In FIGS. 20-21, the package assembly 600 includes an insert 648 having a central cut-out portion 660 that accommodates the head 618. The insert 648 is removably attached to the toothbrush 612. The insert has side panels 662 on opposite sides of the head 618 and the second demonstration element 644 thereon. In addition, it is understood that the first demonstration elements 640 are positioned on the base 634 underneath the second demonstration elements 644. As shown in FIG. 21, the base member 634 may also have a channel 670 formed therein that accommodates the toothbrush 612. The package assembly 700 shown in FIGS. 22 and 23 has structure similar to the package assembly 600 in FIGS. 20-21. The insert 748 may include a plurality of stripes 760 on opposite sides of the head 718. It is understood that vibratory movement can be provided with the package assemblies 600, 700 in FIGS. 20-23 to produce visual effects as described above. FIG. 24 shows another package assembly 800 having an insert 848 configured similarly to the insert 548 in FIG. 18. The insert 848 can include a demonstration element 844 that could take the form of a dot design. Alternatively, the insert 848 can be constructed to have a plurality of particles housed therein. The particles are agitated upon activating the toothbrush 812 via the user input 832 thereby producing a visual effect.

Figure 25:
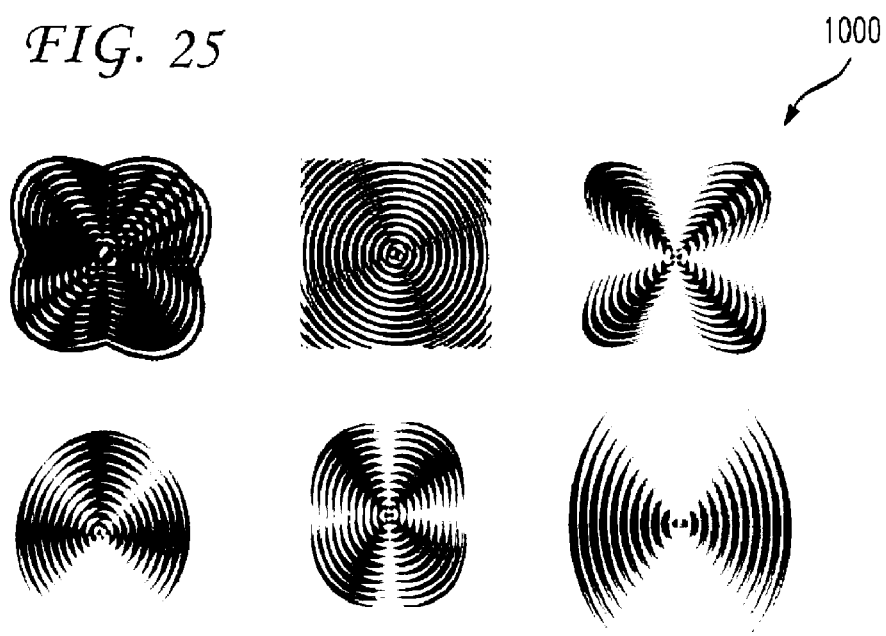
FIG. 25 shows a series of illustrative patterns that may be used in the toothbrush package assembly of the present invention.
Figure 26:
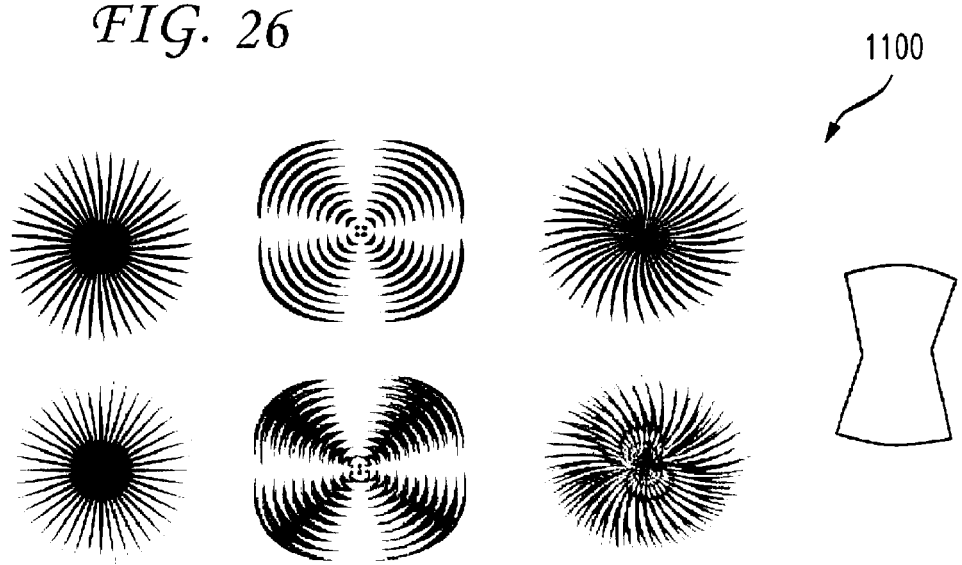
FIG. 26 shows another series of illustrative patterns that may be used in the toothbrush package assembly of the present invention.

FIGS. 25 and 26 display additional patterns 1000, 1100 having different visual illustration features that may be used with the package assemblies and oral care implement demonstration assemblies of the present invention. The patterns can provide a visual effect such a Moiré effect. Other visual effects can be provided that do not rely on a Moiré effect, but may demonstrate features, traits or characteristics of the contained product. In addition, a visual effect can be produced by providing relative movement between the elements of patterns such as shown in FIGS. 25 and 26. It is further understood that multiple visual effects can be produced simultaneously if desired such as when activating the user input 132 in FIG. 11. It is also understood that the package assembly of the present invention can be utilized with a variety of contained products. An exemplary construction has been described herein taking the form of an oral care implement vibration demonstration assembly. A toothbrush has been used by way of example, but it is understood that the package assembly could be used with a variety of different types of oral care implements. The indicia is structured to produce a visual impact to a consumer viewing the package. The indicia can be further manipulated such as by providing relative movement between visual demonstration elements of the indicia, thus providing even greater impact and visual effect.

In one construction, the relative movement is achieved in response to a vibratory input to the contained product such as the toothbrush. The input could also take other forms to provide relative movement of the elements. For example, user input 32, 132, 232, 432, 532, 632 could be connected to a corresponding input device (e.g., button) provided off the toothbrush in a remote manner. The off-toothbrush button could be wired to the respective toothbrush to activate vibration aspect remotely. In one example, a point of display system could be used. In addition, it is understood that the various features of the several different constructions disclosed can be combined.

The package assembly of the present invention demonstrates functionality of a contained product such as a powered toothbrush in a readily perceivable fashion. In addition, with the particular indicia used, demonstrating use of the toothbrush is achieved by visually depicting a toothbrush moving proximate an oral cavity. Thus, this visual effect relates to the actual use environment of the toothbrush itself. Such an active demonstration provides enhanced package assembly features. The overall visual demonstration elements utilized provide a more dynamic visual impact for a consumer viewing the product in the package assembly.

While the invention has been described with respect to specific examples including presently preferred modes of carrying out the invention, those skilled in the art will appreciate that there are numerous variations and permutations of the above described systems and techniques. Thus, the spirit and scope of the invention should be construed broadly as set forth in the appended claims.

We claim:

1. A package for a product, comprising:

a base member having indicia associated therewith; and a powered product contained in the package;

wherein the package further comprises a cover and an insert with a pair of side panels, wherein the indicia comprises a first demonstration element on the cover and a second demonstration element on the insert which is adapted to be mounted on the product via the pair of side panels, and wherein in response to a vibratory input provided by the powered product, the second demonstration element moves independently of the cover and the indicia produces a visual effect indicative of movement associated with the powered product.

2. The package of claim 1 wherein the visual effect is a Moiré effect.

3. The package of claim 1 wherein the indicia comprises a first demonstration element in the form of an oral cavity image and a second demonstration element in the form of a toothbrush image such that in response to the vibratory input, the toothbrush image moves proximate the oral cavity image; wherein the toothbrush image overlays the oral cavity image.

4. A package system, comprising:

a housing containing a powered oral care implement; and an indicia operably associated with the housing, the indicia having a first element containing a marking and a second element containing a marking wherein relative movement between the elements causes the markings to produce a visual effect to a viewer;

wherein the first element is on a transparent cover of the housing and the second element is on an insert which is adapted to be mounted on the powered oral care implement contained by the housing by a pair of side panels of the insert, and wherein the second element is moved relative to the first element and the second element in moved independent of the housing.

5. The package of claim 4 wherein the second element is moved in response to an input adapted to be provided by the powered oral care implement contained by the housing.

6. The package of claim 4 wherein the relative movement is provided by a vibratory input adapted to be provided by the powered oral care implement contained by the housing.

7. The package of claim 4 wherein the relative movement of the markings causes the markings to produce a visual effect taking the form of motion.

8. The package of claim 4 wherein the visual effect is viewable through the cover.

9. The package of claim 4 wherein the first element is in the form of an oral cavity image and the second element is in the form of a toothbrush image wherein the visual effect produced from the relative movement between the elements is the toothbrush image moving proximate the oral cavity image.

10. The package of claim 9 wherein the relative movement is provided by a vibratory input adapted to be provided by the powered oral care implement contained by the housing.

11. The package of claim 4 wherein the first element is in the form of an oral cavity and the second element is in the form of a toothbrush image wherein the visual effect produced from the relative movement between the elements is the toothbrush image moving proximate the oral cavity.

12. The package of claim 11 wherein the relative movement is provided by a vibratory input adapted to be provided by the powered oral care implement contained by the housing.

* * * * *